United States Patent [19]

McComb et al.

[11] 4,323,785

[45] Apr. 6, 1982

[54] METHOD OF AND APPARATUS FOR OBSERVING SHEET SURFACES FOR TRACES OF FLUORESCENT MATERIALS THEREON

[75] Inventors: Walter D. McComb, Oregon; Andrew W. Rudolph, Elmore, both of Ohio

[73] Assignee: Libbey-Owens-Ford Company, Toledo, Ohio

[21] Appl. No.: 150,329

[22] Filed: May 16, 1980

[51] Int. Cl.³ ............................................ G01N 21/64
[52] U.S. Cl. ............................... 250/461 R; 250/302; 250/561
[58] Field of Search ................... 250/302, 358 R, 359, 250/360, 372, 461 R, 561

[56] References Cited

U.S. PATENT DOCUMENTS 3,675,015  7/1972  Geib ..................................... 250/302
3,755,674  8/1973  Murray et al. ...................... 250/372
3,839,637  10/1974  Willis ................................... 250/302
3,952,196  4/1976  Larsen ................................. 250/372

Primary Examiner—Davis L. Willis
Attorney, Agent, or Firm—Collins, Oberlin & Darr

[57] ABSTRACT

An inspection system for ascertaining the surface of a glass sheet that contacted the molten metal bath during production of the glass by the float process and thus has traces of fluorescent metal or metal oxides thereon. The system employs a device for sensing the presence of a glass sheet and activating an ultraviolet light, which is modulated and illuminates the surface of the glass sheet. A visible light detector intercepts light fluorescing from the illuminated sheet surface, producing a signal which is processed by an electronic network for indicating the presence of metallic oxides on the sheet surface. When fluorescence is detected the ultraviolet light is extinguished and when fluorescence is not detected an alarm is activated.

17 Claims, 3 Drawing Figures

METHOD OF AND APPARATUS FOR OBSERVING SHEET SURFACES FOR TRACES OF FLUORESCENT MATERIALS THEREON

BACKGROUND OF THE INVENTION

1. Field of the Invention

This invention generally relates to the field of inspection and, more particularly, to a method of and apparatus for inspecting a glass surface for the presence or nonpresence of traces of metal or metallic oxides on the glass surface.

2. Description of the Prior Art

As is well known, flat glass is commonly produced by the float process, such as illustrated and described in U.S. Pat. No. 3,743,495, issued on July 3, 1973. As there explained, the manufacture of flat glass by the float process involves delivering molten glass at a controlled rate onto a relatively wide bath of molten metal (usually tin) and advancing it along the surface of the bath under physical and thermal conditions which (1) assure that a layer of molten glass will be established on the bath, (2) that the glass in the layer can flow laterally to develop on the surface of the metal bath a buoyant body of molten glass of stable thickness, and (3) that the buoyant body in ribbon form will be continuously advanced along the bath and sufficiently cooled as it advances to permit it to be taken unharmed out of the bath by mechanical conveying means.

In this process, traces of metal or metallic oxides form on the bottom surface of the glass ribbon as it is removed from the molten bath. However, these oxides are substantially invisible to the naked eye and do not present any deleterious effects to the end use of the glass. On the other hand, one of the advantages of float glass is that it is formed with the desired surface finish and so need not be ground and polished. However, while such glass may have excellent optical quality it has been found that the bottom surface of the glass ribbon, that is, the surface in contact with the metallic bath during formation and having the metallic oxides thereon, has a greater degree of planimetry than the top surface of the glass ribbon.

As is well known, in the manufacture of laminated glass products it is desirable to have the surfaces with the better planimetry on the outer surfaces of the end product. In such units the glass surfaces laminated to the plastic interlayer as well as irregularities thereon are in effect eliminated and the optical quality of the finished unit is determined by the outwardly facing surfaces. Thus, in a manufacturing line it is desirable to have the high quality surfaces of the glass sheets facing in a known direction. In view of the foregoing discussion, the surfaces of glass sheets may be continuously inspected for the presence or nonpresence of metallic oxides thereon for determining the better quality surface of the glass sheets. Accordingly, during the processing of glass sheets, corrective action can be immediately and/or automatically taken in the manufacturing line to insure that the better quality surfaces of the glass sheets face in one direction.

SUMMARY OF THE INVENTION

It has been found that ultraviolet light modulated at approximately 22 Hertz, used in conjunction with optical filters that block most of the visible light wavelengths and photocells combined with an amplifier tuned to the same frequency to respond to the ultraviolet light, detects fluorescence of metal or metallic oxides on surfaces of substrates.

Thus, according to the present invention, ultraviolet light modulated at the prescribed frequency is directed against the surfaces of glass sheets for causing any metallic oxides thereon to fluoresce, and an electronic network processes the signals produced in response to the fluorescence to indicate the metallic oxides. Also, the electronic network is adapted to produce an alarm if traces of metallic oxides are not present on the glass surfaces and/or if the ambient light is of sufficient magnitude to interfere with the detection of fluorescence.

A preferred method of inspecting glass surfaces for the presence or nonpresence of metallic oxides thereon generally contemplates the steps of (1) sensing the presence of a glass sheet for energizing an ultraviolet light source, (2) filtering the ultraviolet light for blocking visible light therefrom, (3) directing the ultraviolet light toward the surface of the glass sheet for causing fluorescence of any metallic oxides thereon, (4) intercepting any fluorescence to produce a signal, (5) processing the signal to extinguish the ultraviolet light when metallic oxides are present on the surface, and (6) initiating an alarm when metallic oxides are not present on the glass surface and/or when ambient light is of sufficient magnitude to interfere with detection of fluorescence.

The apparatus employed to practice this method generally comprises a fluorescent light source for illuminating the surfaces of the glass sheet, a sensor for sensing the presence of a glass sheet and energizing the fluorescent light, optical filters for blocking visible light from the fluorescent light, a light detection device for intercepting fluorescence, and an electronic network for extinguishing the ultraviolet light in the presence of fluorescence and initiating an alarm in the nonpresence of fluorescence and/or in the presence of excessive ambient light.

OBJECTS AND ADVANTAGES

It is, therefore, an object of this invention to provide a new and improved type of automatic surface identification system.

Another object of this invention is to provide a surface identification system which is highly reliable, versatile and relatively simple in design.

Yet another object of this invention is to provide a method of and apparatus for detecting traces of metal or metallic oxides on sheet surfaces wherein the oxides are substantially undetectable by the naked eye.

Other objects and advantages will become more apparent during the course of the following description, when taken in connection with the accompanying drawings.

BRIEF DESCRIPTION OF THE DRAWINGS

In the drawings wherein like numerals are employed to designate like parts throughout the same.

DESCRIPTION OF THE PREFERRED EMBODIMENT

Figure 1:
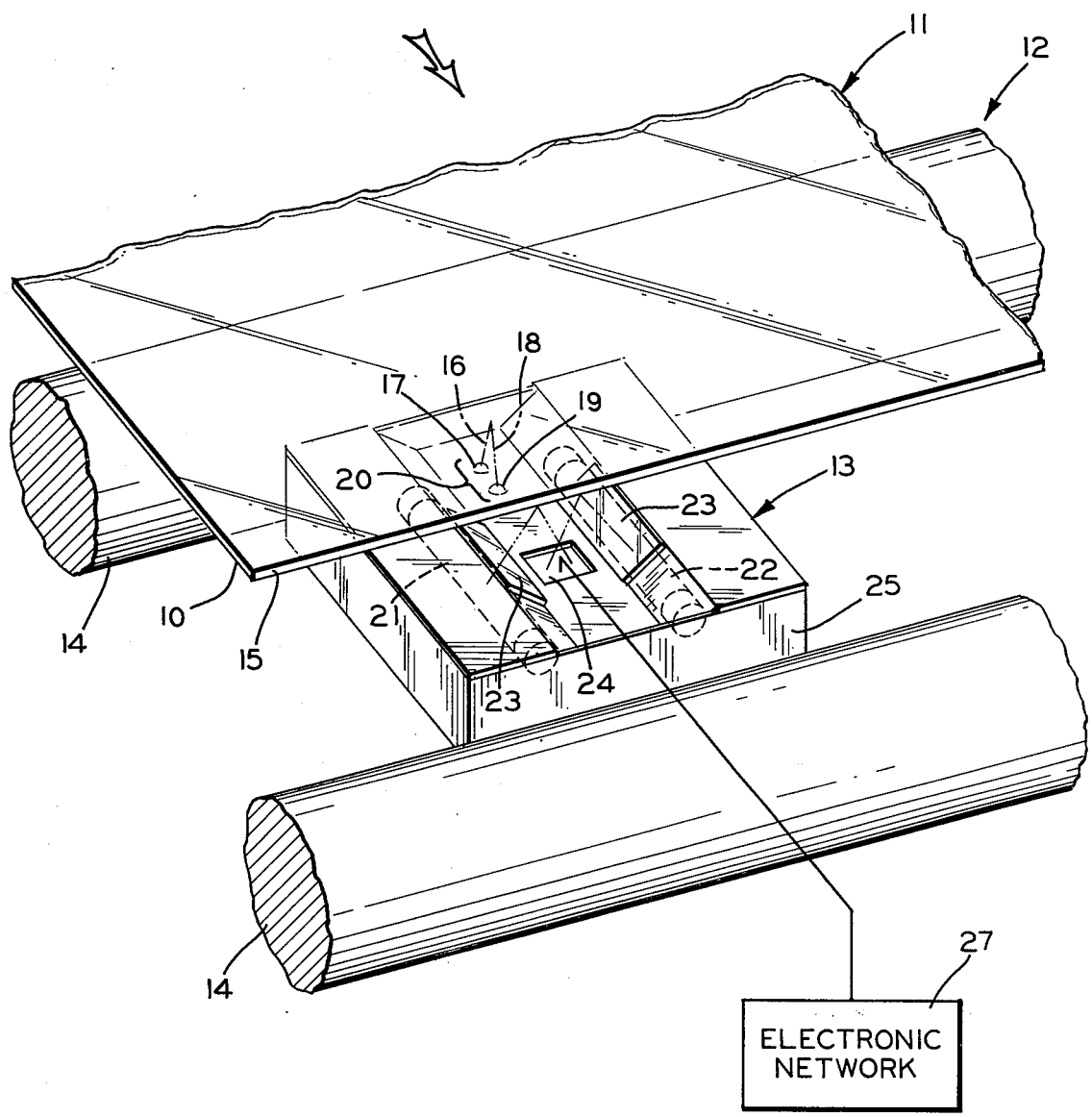
FIG. 1 is a perspective view illustrating one manner of employing the surface identification system including a detector unit embodying the invention.

For convenience and as illustrated in FIG. 1, the surface identification system according to the invention will be described with reference to the inspection of the bottom surfaces 10 of block size glass sheets 11 for the presence or nonpresence of traces of metallic oxides thereon as the sheets 11 move along a roll conveyor 12 over a detector unit, designated in its entirety by the reference numeral 13 and forming part of the inspection system. In this instance, the detector unit 13 is mounted between a pair of adjacent rolls 14 of the conveyor 12. However, it is to be understood that the detector unit 13 may be mounted so as to observe the top surfaces of the glass sheets and also may be employed with other types of material handling equipment.

Still referring to FIG. 1, as one of the sheets 11, whose bottom surface is to be observed, moves along the conveyor 12 to a position above the detector unit 13, its leading edge 15 intercepts a light beam 16 emitting from a light source 17 to produce a reflected light beam 18. The reflected light beam 18 impinges on a photocell 19 which thereby enables the inspection system to begin an operating cycle as will be described hereinafter. When the trailing edge (not shown) of the glass sheet 11 clears a light beam 18, the output signal from the photocell 19 is terminated to end the operating cycle of the inspection system, the light source 17 and photocell 19 constituting a sensor device 20 for sensing the presence of the glass sheet 11.

Figure 2:
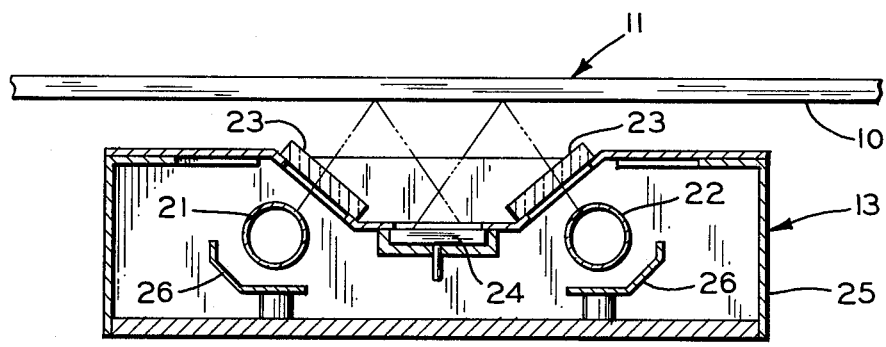
FIG. 2 is an enlarged, cross sectional view of the detector unit illustrated in FIG. 2.

Referring now to FIGS. 1 and 2, the detector unit 13, besides including the sensor 20, also includes an ultraviolet light source comprising a pair of fluorescent mercury lamps 21 and 22, an optical filter 23 for each lamp and a silicon photocell 24. An opaque enclosure 25 containing the above-mentioned elements surrounds the lamps 21 and 22 for preventing ambient light from interfering with their function of illuminating the bottom surface 10 of the glass sheet 11 with ultraviolet light. Ultraviolet light, of course, is not transmitted by the glass sheet so that the top surface will not be illuminated.

More specifically and as best illustrated in FIG. 2, each lamp 21 and 22 is mounted within the enclosure 25 above a reflector 26 so that the emitted light passes through the optical filters 23. The filters 23 block the visible light wavelengths and pass ultraviolet light energy modulated at about 22 Hertz. The filters 23 are so arranged to pass light towards the bottom surface 10 of the glass sheet 11 and the light fluorescing from the surface 10 is reflected downwardly to the photocell 24. Interference by surrounding ambient light is minimized by closely spacing the detector unit 13 to the bottom surface 10 of the glass sheet 11, preferably about 0.5 inch (12.7 mm) therefrom.

When the bottom surface of the glass sheet 11 has traces of metal or metallic oxides thereon, the modulated ultraviolet energy will cause the metallic oxides to fluoresce and the resultant visible light will be detected by the photocell 24 to produce a signal which is transmitted to an electronic network 27 constituting the balance of the inspection system. When the surface of the glass sheet 11 does not have traces of metallic oxide thereon, that is, the metallic oxides appear on the upper surface of the sheet 11, little or no ultraviolet energy will be transmitted through the sheet and thus, no fluorescence will occur. Thus, no fluorescent light will be detected by the photocell 24 and no signal will be trasmitted to the electronic network 27 by photocell.

Generally speaking, the electronic network 27, composed of a novel arrangement of commercially available devices, may be most conveniently described as being arranged in three component circuits, namely a cycling circuit 28 for beginning and ending an inspection cycle, a checking circuit 29 for monitoring ambient light and a signal recognition circuit 30 for monitoring signals from the photocell 24.

Figure 3:
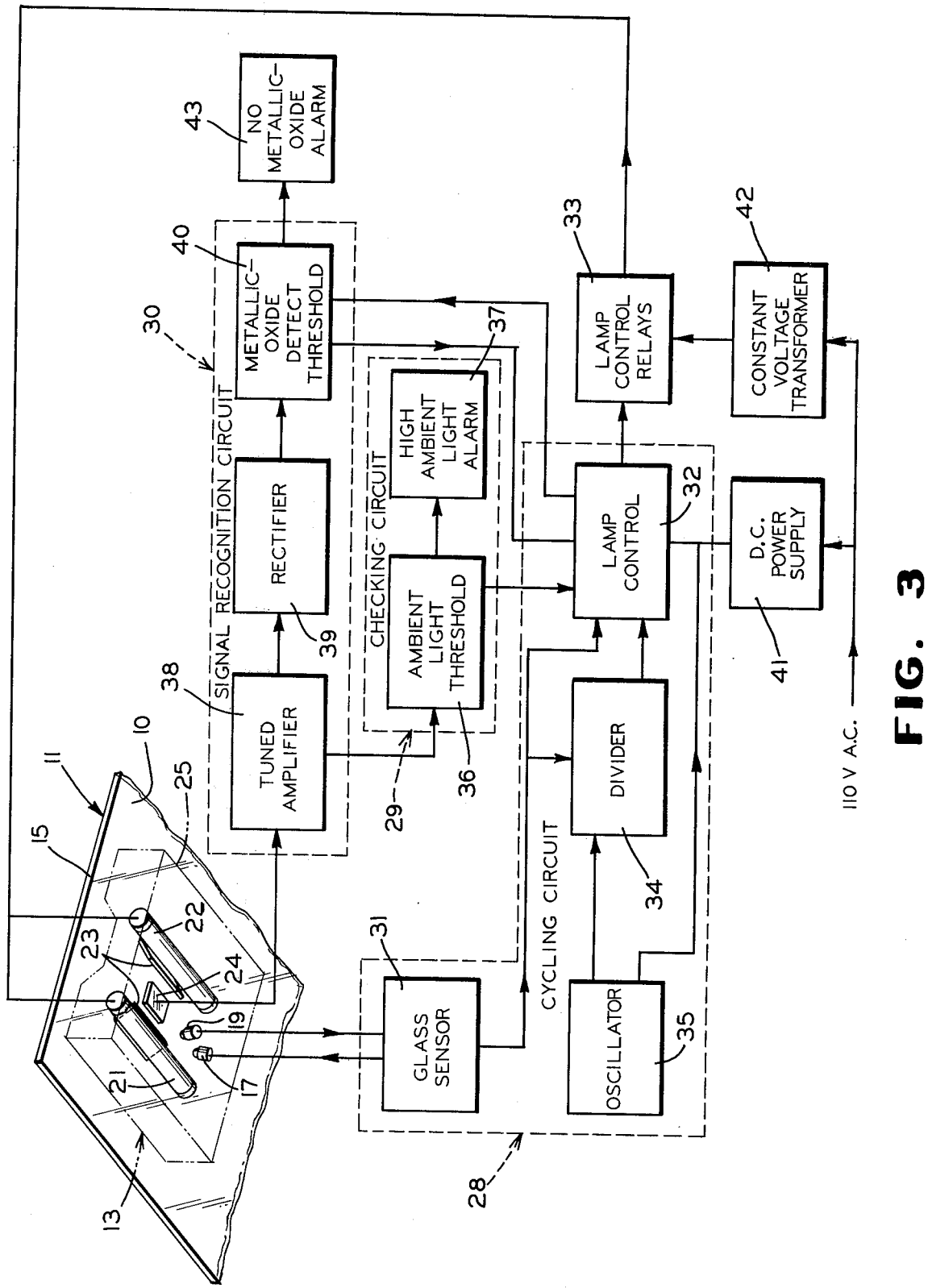
FIG. 3 is a diagrammatic block view of the electronic network employed in the preferred embodiment of the invention.

Referring now to FIG. 3, the cycling circuit 28 generally includes a glass sensor 31 that is activated and deactivated by the sensor device 20, a lamp control unit 32 for controlling the operation of one or more lamp control relays 33, a divider 34 and an oscillator 35, the latter two units timing the operation of the lamp control unit 32. Accordingly, when the glass sensor 31 is activated by the photocell 19, it transmits a signal voltage to the lamp control unit 32 and the divider 34 whereby the signal outputted from the lamp control device places the lamps 21 and 22 in a start mode which lasts for approximately one (1) second before the lamps are lighted.

The checking circuit 29 generally includes an ambient light threshold unit 36 for monitoring any signal from the photocell 24 initiated by ambient light and a high ambient light alarm unit 37 such as a buzzer or light device which is activated when the magnitude of the ambient light is above a predetermined threshold level.

The signal recognition circuit 30 generally includes an amplifier 38 tuned to 22 Hertz which amplifies the signals outputted from the photocell 24, a rectifier 39 for converting the received signals to DC and a metallic oxide detect threshold unit 40, which transmits a signal to the lamp control unit 32 for extinguishing the lamps 21 and 22 when metallic oxides are detected.

The purpose of modulating the lamps 21 and 22 and tuning the amplifier 26 to a frequency of 22 Hertz is to minimize interference from ambient light which can mask the fluorescence from the metallic oxide on the glass surface.

A DC power supply unit 41 is provided to energize the units of the cycling circuit 28, the checking circuit 29 and the signal recognition circuit 30 with DC voltage.

A constant voltage transformer 42 regulates the 110 AC line voltage to a stable voltage and passes this voltage through the relays 33 for energizing and deenergizing the lamps 21 and 22. The lamps 21 and 22 are energized and deenergized for each inspection cycle, that is, for the individual inspection of each glass sheet 11 so as to extend the life of the optical filters 23 as the filters slowly deteriorate from exposure to ultraviolet light.

In operation, when a glass sheet 11 having traces of metallic oxides on the surface adjacent the detector unit 13 traverses the detector unit, an inspection cycle is initiated by the photocell 19 sending a signal to the glass sensor 31 which, in turn, transmits a signal to the lamp control unit 32 and the divider 34 for placing the lamps 21 and 22 in their start mode which lasts for about one (1) second. Near the end of this time, the photocell 24 is checked to see if ambient light is causing it to emit a signal to the ambient light threshold unit 36 via the amplifier 38. If the signal from the amplifier 38 exceeds the predetermined threshold level of the ambient light threshold unit 36, the ambient light alarm 37 is activated and the threshold unit 36 transmits a signal to the lamp control unit 32 which initiates a non-metallic oxide alarm 43 via the metallic oxide threshold device 40. This set of conditions inhibits the inspection system from looking for metallic oxides, that is, the ambient light is at a level exceeding the system's light operating level and will mask the light fluorescing from the metallic oxides.

Also, the initiation of the non-metallic oxide alarm 43 may be an indication that the optical filters 23 have deteriorated to a point where they no longer satisfactorily perform their filtering function.

When the signal from the amplifier 38 is acceptable by the ambient light threshold unit 36, after a delay of about one (1) second the lamp control unit 32 transmits a signal to the lamp control relay 33 lighting the lamps 21 and 22 and to the metallic oxide detect threshold unit 40, enabling it to receive a signal from the rectifier 39. When the detect threshold unit 40 receives a signal from the rectifier 39, a signal is transmitted to the lamp control unit 32 which in turn extinguishes the lamps 21 and 22 via the lamp control relay 33 and no signals are outputted by the inspection system. In otherwords, when metallic oxides are detected on the glass surface 10, the glass sheet 11 is "passed" by the inspection system. On the other hand, when no metallic oxides are detected one second after lighting the lamps 21 and 22, the alarm 43 is activated and the glass sheet is "rejected".

After the trailing edge of the glass sheet 11 traverses the sensor device 20, the signal activating the cycling circuit 28 is terminated and all the units are reset for the next inspection cycle.

It is to be understood that the form of the invention herewith shown and described is to be taken as an illustrative embodiment only of the same, and that various changes in the shape, size and arrangement of the parts as well as various procedural changes, may be resorted to without departing from the spirit of the invention or the scope of the subjoined claims.

We claim:

1. A method of insuring that sheet articles having traces of fluorescent material deposited on one surface during their formation are oriented with said one surface in a prescribed direction as they advance along a conveyor, comprising the steps of
    a. generating a signal in response to the arrival of each said sheet article at an inspection station along said conveyor;
    b. utilizing said signal to initiate an inspection cycle including;
    c. placing an ultraviolet light source in a delayed start mode;
    d. checking a photocell positioned to receive fluorescent light from said sheet article for exposure to excess ambient light and activating an alarm in response to such excess light;
    e. in the absence of excess ambient light, starting said ultraviolet source to expose the surface of said sheet article to ultraviolet light;
    f. generating a signal from said photocell in response to fluorescent light from said surface, with no signal being generated in the absence of fluorescent light; and
    g. utilizing the signal and lack of a signal from said photocell to differentiate between the two surfaces of said sheet article and activate an alarm to identify an improperly oriented sheet.

2. A method of insuring that the surface of a sheet article is oriented in a prescribed direction as claimed in claim 1, including the step of modulating the ultraviolet light to a frequency of about 22 Hertz.

3. A method of insuring that the surface of a sheet article is oriented in a prescribed direction, as claimed in claim 1, wherein the fluorescent material is tin oxide.

4. A method of insuring that the surface of a sheet article is oriented in a prescribed direction as claimed in claim 1, wherein the ultraviolet light is produced by mercury lamps.

5. A method of insuring that the surface of a sheet article is oriented in a prescribed direction as claimed in claim 4, including the step of filtering the ultraviolet light.

6. An apparatus for inspecting the surface of a sheet article for the presence of traces of fluorescent material thereon comprising:
    a. means for illuminating the surface of the sheet article with a source of ultraviolet light and thereby causing fluorescence of any metallic oxides;
    b. article sensing means for activating said illuminating means;
    c. light detection device for intercepting fluorescence from any metallic oxide; and
    d. a logic network connected to said article sensing means and said light detection device for extinguishing the source of ultraviolet light when fluorescence is detected and initiating an alarm when fluorescence is not detected.

7. An apparatus for inspecting the surface of a sheet article as claimed in claim 6, wherein said illuminating means comprises at least one ultraviolet lamp and said light detection device comprises a photocell.

8. An apparatus for inspecting the surface of a sheet article as claimed in claim 7, wherein said ultraviolet lamp is a mercury lamp and said photocell is a silicon photocell.

9. An apparatus for inspecting the surface of a sheet article as claimed in claim 8, including means for filtering said ultraviolet lamp.

10. An apparatus for inspecting the surface of a sheet article as claimed in claim 6, including means for modulating the ultraviolet light to a frequency of 22 Hertz.

11. An apparatus for inspecting the surface of a sheet article as claimed in claim 6, including means for beginning and ending an inspection cycle of said logic network.

12. An apparatus for inspecting the surface of a sheet article as claimed in claim 11, wherein said means for beginning and ending the inspection cycle comprises a sensor device including a light source and a photocell for producing a signal in conjunction with the leading edge and the trailing edge of the sheet article.

13. In an apparatus for inspecting the surface of a sheet article for the presence of metallic oxides thereon as said article advances along a conveyor, wherein an ultraviolet light source illuminates the surface and causes the metallic oxides to fluoresce, the improvement comprising:
    a. a sensor for detecting the presence of the sheet article;
    b. a cycling circuit activated by said sensor for controlling the operation of said ultraviolet light lamp;
    c. a light detecting device for intercepting fluorescence from the metallic oxides;
    d. a signal recognition circuit for monitoring fluorescence and operated by said light detecting device; and e. a checking circuit for monitoring ambient light and controlling operation of said signal recognition circuit, whereby when fluorescence from the metallic oxides is detected, said ultraviolet lamp is extinguished and when fluorescence is not detected, an alarm signal is initiated.

14. An apparatus for inspecting the surface of a sheet article as claimed in claim 13, wherein said sensor comprises a light source which emits a light beam which is reflected by the glass article and a photocell for receiving the reflected light beam for producing a signal and activating said cycling circuit.

15. An apparatus for inspecting the surface of a sheet article as claimed in claim 13, wherein said cycling circuit includes a lamp control unit and a timing means comprising a divider and an oscillator for delaying the action of said lamp control unit.

16. An apparatus for inspecting the surface of a sheet article as claimed in claim 13, wherein said light detecting device comprises a photocell and said signal recognition circuit comprises an amplifier, a rectifier and a metallic oxide threshold unit for receiving and processing a fluorescence signal from said photocell.

17. An apparatus for inspecting the surface of a sheet article as claimed in claim 13, wherein said checking circuit includes an ambient light threshold unit and an alarm.

* * * * *